United States Patent
Kato et al.

(10) Patent No.: US 10,384,998 B2
(45) Date of Patent: Aug. 20, 2019

(54) METHOD FOR PRODUCING PROPIONALDEHYDE

(71) Applicants: Mitsubishi Chemical Corporation, Chiyoda-ku (JP); TOKUSHIMA UNIVERSITY, Tokushima-shi (JP)

(72) Inventors: Yuki Kato, Chiyoda-ku (JP); Wataru Ninomiya, Chiyoda-ku (JP); Shigeru Sugiyama, Tokushima (JP)

(73) Assignees: Mitsubishi Chemical Corporation, Chiyoda-ku (JP); TOKUSHIMA UNIVERSITY, Tokushima-shi (JP)

( * ) Notice: Subject to any disclaimer, the term of this patent is extended or adjusted under 35 U.S.C. 154(b) by 0 days.

(21) Appl. No.: 16/202,914

(22) Filed: Nov. 28, 2018

(65) Prior Publication Data

US 2019/0135722 A1 May 9, 2019

Related U.S. Application Data

(63) Continuation of application No. PCT/JP2017/020095, filed on May 30, 2017.

(30) Foreign Application Priority Data

May 31, 2016 (JP) ................. 2016-108673

(51) Int. Cl.
| | |
|---|---|
| C07C 45/00 | (2006.01) |
| B01J 29/00 | (2006.01) |
| C07C 45/51 | (2006.01) |
| B01J 29/04 | (2006.01) |
| C07C 47/02 | (2006.01) |

(52) U.S. Cl.
CPC ........... *C07C 45/511* (2013.01); *B01J 29/041* (2013.01); *C07C 47/02* (2013.01)

(58) Field of Classification Search
CPC .............................. C07C 45/511; B01J 29/041
See application file for complete search history.

(56) References Cited

U.S. PATENT DOCUMENTS

2011/0257355 A1 10/2011 Moriguchi et al.
2015/0343429 A1 12/2015 Sugiyama et al.

FOREIGN PATENT DOCUMENTS

| JP | 2010-180156 | 8/2010 |
|---|---|---|
| WO | WO 2010/074177 A1 | 7/2010 |
| WO | WO 2014/123095 A1 | 8/2014 |

OTHER PUBLICATIONS

International Search Report dated Aug. 22, 2017 in PCT/JP2017/020095, filed on May 30, 2017.
Written Opinion dated Aug. 22, 2017 in PCT/JP2017/020095, filed on May 30, 2017.
Arpe,H. "Hydroformylation of Olefins, Synthesis Involving Carbon Monoxide" Industrial Organic Chemistry, 4th Completely Revised Edition Wiley-VCH GmbH & Co. KGaA, Germany, 2003, pp. 4.
Ghammamy, S. et al. "Triethylammonium Fluorochromate—A New, Mild, Stable, and Inexpensive Chromium (VI) Oxidant*" Russian Journal of Organic Chemistry, Vo. 41, No. 12, 2005, pp. 3.
Inagaki et al., "Synthesis of Highly Ordered Mesoporous Materials from a Layered Polysilicate," J. Chem. Soc., Chem. Commun. , No. 8, 1993, pp. 3.
Possato, L. et al., "A comparative study of glycerol dehydration catalyzed by micro/mesoporous MFI zeolites," Journal of Catalysis, vol. 300, 2013, pp. 11.

*Primary Examiner* — Sikarl A Witherspoon
(74) *Attorney, Agent, or Firm* — Oblon, McClelland, Maier & Neustadt, L.L.P.

(57) ABSTRACT

To provide a method for producing propionaldehyde directly from glycerol with high yield, gasified glycerol is brought into contact with a silica-type regular mesoporous body. More specifically, gasified glycerol is supplied to a catalyst layer containing a regular mesoporous body while heating the catalyst layer at a temperature ranging from 200 to 800° C. in such a manner that a W/F value can fall within the range from 0.001 to 1000 g·min/ml inclusive wherein W represents an amount (g) of a catalyst and F represents a supply rate (ml/min) of supplied glycerol.

7 Claims, No Drawings

METHOD FOR PRODUCING PROPIONALDEHYDE

TECHNICAL FIELD

The present invention relates to a process for producing propionaldehyde.

BACKGROUND ART

Propionaldehyde is used as a solvent raw material, a chemical intermediate product, a solvent for production of pharmaceutical intermediates, etc., and it is an important substance in the chemical industry. Propionaldehyde can be obtained by a hydroformylation reaction of ethylene (Non-Patent Document 1). It can also be obtained by partial hydrogenation of allyl alcohol as a raw material.

However, the construction of a hydroformylation reactor requires enormous capital investment. In addition, when propionaldehyde is obtained by partial hydrogenation using allyl alcohol as a raw material, part of the carbonyl moiety is also hydrogenated and the selectivity of the target product may be lowered in some cases. There is also known a method of dehydrogenating 1-propanol to obtain propionaldehyde (Non-Patent Document 2), but there is a problem in supplying 1-propanol as a raw material.

Under such circumstances, a method of synthesizing propionaldehyde by using 1,2-propanediol as a raw material and using a heteropolyacid or heteropolyacid-catalyst carrier complex as a catalyst has been studied. (Patent Document 1).

The present inventors have proposed a method for producing a saturated aldehyde from 1,2-alkanediol in the presence of a regular mesoporous material (Patent Document 2). This method is particularly a method of synthesizing propionaldehyde from 1,2-propanediol.

CITATION LIST

Patent Document

Patent Document 1: JP 2010-180156 A
Patent Document 2: WO 2014/123095 A1

Non-Patent Document

Non-Patent Document 1: Arpe, H J. Industrial Organic Chemistry, 4th Complexity Revised Edition; Wiley-VCH GmbH & Co. KGaA, Germany, 2003
Non-Patent Document 2: Russian Journal of Organic Chemistry (2005), 41, (12), 1752-1754

SUMMARY OF THE INVENTION

Problem to be Solved by the Invention 1,2-Propanediol is made from glycerol as a raw material. However, considering the use of biomass-derived glycerol, it is desired to directly synthesize propionaldehyde from glycerol rather than via 1,2-propanediol.

However, there is no prior manufacturing method aimed at producing propioldehyde directly from glycerol. Although it was confirmed that a small amount can be obtained as a byproduct of the oxidation reaction of glycerol in part, a method for producing it as a main product has not been established.

It is an object of the present invention to provide a method capable of directly producing propionaldehyde from glycerol with high yield.

Means for Solving Problem

The present invention includes the following aspects [1] to [7]:
[1] A process for producing propionaldehyde wherein propionaldehyde is directly produced from glycerol, which comprises contacting gasified glycerol with a silica-based regular mesoporous material.
[2] The method for producing propionaldehyde according to [1], wherein the regular mesoporous material has a pore size of 2.0 nm or more and 10.0 nm or less.
[3] The method for producing propionaldehyde according to [1] or [2], wherein the regular mesoporous material is FSM-16.
[4] The method for producing propionaldehyde according to any one of [1] to [3], wherein the glycerol is biomass-derived glycerol.
[5] The method for producing propionaldehyde according to any one of [1] to [4], wherein the gasified glycerol is supplied to the catalyst layer containing the regular mesoporous material.
[6] The method for producing propionaldehyde according to [5], wherein the glycerol is passed through the catalyst layer heated in the range of 200° C. to 800° C.
[7] The method for producing glycerol according to any one of [1] to [3], wherein the supply of glycerol is carried out in a range of 0.001 g·min/ml or more and 1000 g·min/ml or less as W/F, where W is an amount (g) of the catalyst and F is a supply rate (ml/min) of the supplied glycerol.

Effects of the Invention

According to the present invention, it is possible to produce propionaldehyde directly from glycerol with high yield.

EMBODIMENTS FOR CARRYING OUT THE INVENTION

In the method according to the present invention, propionaldehyde is produced from glycerol in the presence of a regular mesoporous material. In the present invention, by using a regular mesoporous material as a catalyst, it is possible to produce propionaldehyde directly from glycerol with high yield.

[Regular Mesoporous Material]

In the present invention, the regular mesoporous material refers to a silica-based material having fine pores with a diameter of 2 to 50 nm and the pores regularly arranged. As the regular mesoporous material according to the present invention, a solid acid catalyst having high acid strength can be used. In general, silica, alumina or the like is used as the solid acid catalyst, but the use of the regular mesoporous material as in the present invention makes it possible to produce propionaldehyde directly from glycerol with high selectivity since hydroxyl groups present inside the regularly arranged mesopores have high performance as an acid catalyst in addition to an increase in the reaction field due to a high specific surface area.

As the regular mesoporous material, for example, a regular mesoporous material synthesized by applying a surfactant to a layered silicate can be mentioned. A regular mesoporous material synthesized by the method described in S. Inagaki et al., J. Chem. Soc., Chem. Commun., No. 8, 680-682 (1993). S. Inagaki et al., J. Chem. Soc., Chem. Commun., No. 8, 680-682 (1993), is a regular mesoporous material synthesized by reacting a layered silicate with a surfactant. The regular mesoporous material thus synthesized has a structure in which the periodically curved silicate sheets are vertically coupled at the convex portions and countless numbers of uniformly aligned pores are present in the gap between the sheets. The pores have a diameter of from 2 to 10 nm and are distributed around a certain diameter in a narrow range.

Examples of the layered silicate used for synthesizing the regular mesoporous material include kanemite ($NaHSi_2O_5.3H_2O$), sodium disilicate crystals ($\alpha,\beta,\gamma,\sigma$-$Na_2Si_2O_5$), makatite ($Na_2Si_4O_9.5H_2O$), ilerite ($Na_2Si_8O_{17}.xH_2O$), magadiite ($Na_2Si_{14}O_{29}.xH_2O$), kenyaite ($Na_2Si_{20}O_{41}.xH_2O$) and the like can be used. Of these, kanemite is preferable as the layered silicate. One or two or more kinds of these layered silicates may be used.

As the surfactant used for synthesizing the regular mesoporous material, chloride, bromide, iodide, hydroxide of alkyltrimethylammonium, dimethyldialkylammonium, alkylammonium, benzylammonium and the like can be used. Among them, a bromide of alkyltrimethylammonium is preferable as a surfactant. The alkyl group in the chloride, bromide, iodide or hydroxide of alkyltrimethylammonium, dimethyldialkylammonium, alkylammonium is preferably a linear or branched alkyl group having 8 to 18 carbon atoms. One or two or more kinds of these surfactants may be used. When alkyltrimethylammonium, for example, is used for the surfactant, the pore diameter can be changed depending on the length of the alkyl chain length. Among them, it is preferable to produce FSM-16, which is a regular mesoporous material from kanemite, using hexadecyltrimethylammonium ($C_{16}H_{33}N(CH_3)_3$).

Examples of the method to synthesize the regular mesoporous material by the reaction of a layered silicate with a surfactant may include a method in which the layered silicate described above is dispersed in a solvent prepared by dissolving a surfactant. The solvent is preferably water but may be a water-alcohol mixed solvent or another solvent. The concentration of the surfactant is preferably from 0.05 to 1 mol/L. With regard to the dispersed amount of the layered silicate, for example, 5 to 200 g of kanemite with respect to 1000 ml of a 0.1 mol/L aqueous solution of a surfactant is preferable. The reaction temperature is preferably from 50 to 150° C. It is preferable to stir the dispersion solution during heating. The pH of the dispersion solution is preferably 10 or more for from 1 to 5 hours at the beginning and 10 or less for the rest of the time. Since the kanemite exhibits alkalinity, the pH of the dispersion solution is 10 or more without adding other alkaline substances in the above-mentioned addition amount range. It is possible to adjust the pH to 10 or more by adding alkaline substances such as sodium hydroxide in a case in which the pH is 10 or less. Thereafter, the pH of the solution can be lowered to 10 or less by adding an acid such as hydrochloric acid. It is preferable to lower the pH of the solution to 8.5. It is possible to obtain a regular mesoporous material which exhibits particularly high crystallinity and heat resistance by the pH control. Thereafter, the solid product is recovered by filtration. The reaction time is preferably from 1 to 20 hours. Meanwhile, the reaction time refers to the time from when the layered silicate and the surfactant are mixed together until when the solid product is filtered. It is possible to obtain a regular mesoporous material exhibiting high heat resistance by repeatedly washing the solid product with deionized water and the like. It is possible to remove the surfactant incorporated in the crystal by calcining the solid product at a temperature of 550° C. or higher or treating with an acid/organic solvent mixed solution after drying the solid product, thereby to obtain a regular mesoporous material. As the calcining condition in the case of performing calcination, it is preferable to heat the solid product for 1 hour or longer under an atmosphere of air, oxygen, nitrogen or the like. In addition, in the case of treating with the acid/organic solvent mixed solution, the mixed solution is preferably a hydrochloric acid/ethanol mixed solution, and other acids and other organic solvents other than hydrochloric acid and ethanol may be used as long as a combination of an acid/an organic solvent.

The regular mesoporous material thus obtained is a regular mesoporous material having a periodic structure. It should be noted that the regular mesoporous material having a periodic structure is confirmed by the existence of one or more X-ray diffraction peaks including the maximum peak at the interplanar spacing d value of 2 nm or more in structural analysis by X-ray. When used in the present invention, the lower limit of the pore diameter of the regular mesoporous material is 2.0 nm or more, more preferably 2.5 nm or more, the upper limit is 10.0 nm or less, and more preferably 5.0 nm or less. In the regular mesoporous silica-based material, hydroxyl groups present on the wall surface of the mesopores are positioned from the wall surface toward the center of the pores, and hydroxyl groups exist at high density in the center of the pores. For this reason, silica-based ordered mesoporous materials are considered to exhibit specific acid strength. When the pore diameter is 2.0 nm or more, the reactant is likely to be taken in the space of hydroxyl groups arranged toward the center. In addition, when the pore diameter is 10.0 nm or less, the range is within a range where the contact between the hydroxyl group and the reactant is sufficiently performed and the space of the hydroxyl group is large so as to be taken the reactant thereinto.

[Method for Producing Propionaldehyde from Glycerol]

The method according to the present invention is carried out by contacting gasified glycerol with a regular mesoporous material. For example, it can be carried out in a gas phase flow system in which glycerol as a raw material is gasified and passed through a catalyst layer containing a regular mesoporous material. Glycerol as a raw material may contain water, and glycerol derived from biomass can be used. Further, an inert gas such as helium or nitrogen can coexist with the raw material gas to be used. Glycerol derived from biomass includes, for example, glycerol separated in the process of producing biodiesel fuel made from waste oil (tallow and edible oil) and may include unconverted fatty acid and the like. In the present invention, even such glycerol derived from biomass can be used as it is without separating impurities.

In the case of carrying out by the above method, the catalyst layer containing a regular mesoporous material is heated. The lower limit of the temperature is 200° C. or higher, and more preferably 350° C. or higher. The upper limit is 800° C. or lower, and more preferably 500° C. or lower. When the temperature of the regular mesoporous material is 200° C. or higher, high catalytic activity can be obtained. In addition, when the temperature of the regular mesoporous material is 800° C. or lower, it is possible to suppress the decrease in the selectivity of the target product and the decrease in catalyst activity due to the thermal decomposition reaction of the raw material.

The reaction pressure can be suitably selected, and is usually 1 MPa or less, and atmospheric pressure is preferable. The reaction can be carried out in a fixed bed flow reaction system in which a mixed gas containing raw material glycerol, an inert gas and the like is passed through a reactor packed with a catalyst.

W/F of the supplied glycerol is preferably 0.001 g·min/ml or more, more preferably 0.01 g·min/ml or more as the lower limit. The W/F is preferably 1000 g·min/ml or less, and more preferably 100 g·min/ml or less as the upper limit. If the W/F is 0.001 g·min/ml or more, the conversion can be preferably maintained at high. In addition, if the reactivity becomes too high, product is also reacted, which causes decrease in selectivity and deterioration of catalyst, so it is preferably 1000 g·min/ml or less. Meanwhile, W is the amount (g) of the catalyst packed in the reaction tube, and F is the supply rate (ml/min) of glycerol supplied to the layer packed with the catalyst. In other words, the W/F is the filled catalyst mass with respect to the feed rate of glycerol fed into the reaction tube, and is calculated by the following equation:

$W/F$=amount (g) of catalyst to be packed/supply rate (ml/min) of glycerol fed into the reaction tube

EXAMPLES

Hereinafter, the present invention will be described in detail by way of Examples and Comparative Examples, but the present invention is not limited to these Examples.

The periodic structure of the regular mesoporous material was confirmed by obtaining the X-ray diffraction peak using a powder X-ray diffractometer (product name: Rigaku RINT 2500 VHF, Rigaku Corporation).

The pore diameter of the regular mesoporous material is calculated from the position of the peak of the pore diameter distribution curve created as follows. The pore diameter distribution curve refers to a curve created by plotting the value (dV/dD) obtained by differentiating the pore volume (V) by the pore diameter (D) with respect to the pore diameter (D). The pore distribution curve was determined by a calculation method of the BJH method after obtaining the nitrogen adsorption isotherm using a gas adsorption apparatus (product name: BELSORP-max, BEL Japan, Inc.).

In the method for producing propionaldehyde, analysis of raw material mixed gas and product was carried out by gas chromatography. From the results of gas chromatography, the conversion of glycerol, the selectivity of propionaldehyde, and the yield of propionaldehyde were determined by the following equations:

Glycerol conversion (%)=$(B/A) \times 100$

Propionic aldehyde selectivity (%)=$(C/B) \times 100$

Propionaldehyde yield (%)=$(C/A) \times 100$

In these equations. A is a mole number of supplied glycerol, B is a mole number of reacted glycerol, and C is a mole number of produced propionaldehyde.

Example 1

For 6 hours, 5.0 g of sodium silicate was calcined at 700° C. The sodium silicate thus calcined was added into 50 mL of distilled water, stirred for 3 hours at room temperature, and filtered, thereby to obtain a paste of kanemite which is a layered silicate. To the kanemite paste thus obtained, 100 ml of 0.1 mol/L aqueous solution of hexadecyltrimethylammonium bromide was added, and the mixture was stirred and maintained for 3 hours at 70° C. At that time, pH was 11.5. Thereafter, the pH thereof was adjusted to 8.5 using a 2 mol/L aqueous solution of hydrochloric acid and subsequently stirred and maintained for 18 hours at 70° C. Thereafter, the resultant was filtered, washed with distilled water several times, and dried, thereby to obtain a precursor of regular mesoporous material FSM-16. The precursor was then calcined for 8 hours at 550° C. in an air atmosphere, thereby to obtain a regular mesoporous material FSM-16.

The result of the structural analysis by X-ray confirmed that the regular mesoporous material thus obtained was a regular mesoporous material having a diffraction peak of the d value at the position of 4.0 nm or more and a periodic structure.

The regular mesoporous material thus obtained was packed in a reaction tube made of quartz and having a diameter of 9 mm and a length of 35 mm, which was installed in a fixed bed flow type reactor. The reaction tube was kept at 400° C. by an electric heating furnace. Then, under atmospheric pressure, oxygen gas was allowed to flow through the reaction tube at a flow rate of 30 ml/min for 1 hour. Thereafter, nitrogen was flowed at a flow rate of 30 ml/min, glycerol was vaporized and supplied to a reaction tube (catalyst layer) packed with regular mesoporous material at a flow rate of 0.2 ml/min together with nitrogen, and propionaldehyde. Each of conditions was set so that W/F was 0.125 g·min/ml.

After 15 minutes from the start of the reaction, the gas at the outlet of the reaction tube was measured by gas chromatography to determine the conversion of glycerol, the selectivity of propionaldehyde and the yield of propionaldehyde. The results are shown in Table 1.

TABLE 1

|  | W/F (g · min/ml) | Pore diameter (nm) | Conversion (%) | Selectivity (%) | Yield (%) |
| --- | --- | --- | --- | --- | --- |
| Example 1 | 0.125 | 2.7 | 100.0 | 31.2 | 31.2 |

As described above, propionaldehyde can be efficiently produced directly from glycerol by using a regular mesoporous material synthesized by reacting a layered silicate with a surfactant.

The invention claimed is:

1. A method for producing propionaldehyde wherein propionaldehyde is directly produced from glycerol, the method comprising contacting gasified glycerol with a silica-based regular mesoporous material.

2. The method for producing propionaldehyde according to claim 1, wherein the regular mesoporous material has a pore size of 2.0 nm or more and 10.0 nm or less.

3. The method for producing propionaldehyde according to claim 1, wherein the regular mesoporous material is FSM-16.

4. The method for producing propionaldehyde according to claim 1, wherein the glycerol is biomass-derived glycerol.

5. The method for producing propionaldehyde according to claim 1, wherein the gasified glycerol is supplied to the catalyst layer containing the regular mesoporous material.

6. The method for producing propionaldehyde according to claim 5, wherein the glycerol is passed through the catalyst layer heated in the range of 200° C. to 800° C.

7. The method for producing glycerol according to claim 5, wherein the supply of glycerol is carried out in a range of 0.001 g·min/ml or more and 1000 g·min/ml or less as W/F, where W is an amount (g) of the catalyst and F is a supply rate (ml/min) of the supplied glycerol.

* * * * *